United States Patent
Fujisawa

(10) Patent No.: US 9,066,654 B2
(45) Date of Patent: Jun. 30, 2015

(54) MEDICAL IMAGE PROCESSING APPARATUS, AN X-RAY CT SCANNER, AND A MEDICAL IMAGE PROCESSING PROGRAM

(75) Inventor: Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 84 days.

(21) Appl. No.: 13/878,516

(22) PCT Filed: Jan. 13, 2012

(86) PCT No.: PCT/JP2012/050563
§ 371 (c)(1),
(2), (4) Date: Apr. 9, 2013

(87) PCT Pub. No.: WO2012/099004
PCT Pub. Date: Jul. 26, 2012

(65) Prior Publication Data
US 2013/0208970 A1     Aug. 15, 2013

(30) Foreign Application Priority Data
Jan. 19, 2011   (JP) ................................. 2011-008632

(51) Int. Cl.
*G06K 9/00*     (2006.01)
*A61B 5/00*     (2006.01)
(Continued)

(52) U.S. Cl.
CPC ............. *A61B 5/0033* (2013.01); *A61B 6/5217* (2013.01); *A61B 6/032* (2013.01);
(Continued)

(58) Field of Classification Search
USPC ............. 378/4, 901; 382/131; 435/1.2, 284.1, 435/297.2; 600/334, 363
See application file for complete search history.

(56) References Cited

U.S. PATENT DOCUMENTS

| 8,010,184 B2 | 8/2011 | Avila et al. |
| 2005/0020903 A1* | 1/2005 | Krishnan et al. ............... 600/407 |
| 2007/0167697 A1* | 7/2007 | Avila et al. ..................... 600/407 |

FOREIGN PATENT DOCUMENTS

| CN | 101011259 A | 8/2007 |
| JP | 2003 70781 | 3/2003 |

(Continued)

OTHER PUBLICATIONS

International Search Report Issued Apr. 17, 2012 in PCT/JP12/050563 Filed Jan. 13, 2012.

(Continued)

*Primary Examiner* — Gregory F Cunningham
(74) *Attorney, Agent, or Firm* — Oblon, McClelland, Maier & Neustadt, L.L.P.

(57) ABSTRACT

A medical image processing apparatus to accurately identify malignant transformations of probable tumors. The medical image processing apparatus including a specifying mechanism and first, second, and third computing mechanisms. The specifying mechanism specifies a probable tumor from medical image data upon receiving the medical image data obtained by imaging a subject by a single medical imaging apparatus. The first computing mechanism calculates morphological information indicating morphological characteristics of a specified probable disease based on this medical image data. The second computing mechanism calculates functional information of the specified probable disease based on this medical image data. The third computing mechanism calculates amount of progress characteristics indicating the extent of the probable disease based on the morphological information and functional information.

11 Claims, 9 Drawing Sheets

(51) Int. Cl.
 *A61B 6/00* (2006.01)
 *A61B 6/03* (2006.01)
 *G06T 7/00* (2006.01)

(52) U.S. Cl.
 CPC ............... *A61B 6/481* (2013.01); *A61B 6/507* (2013.01); *G06T 7/0012* (2013.01); *G06T 2200/24* (2013.01); *G06T 2207/10081* (2013.01); *G06T 2207/30064* (2013.01); *G06T 2207/30104* (2013.01)

(56) References Cited

FOREIGN PATENT DOCUMENTS

| | | |
|---|---|---|
| JP | 2004-222864 A | 8/2004 |
| JP | 2005 224429 | 8/2005 |
| JP | 2006 187412 | 7/2006 |
| JP | 2006187412 A * | 7/2006 ............... G06T 1/00 |
| JP | 2007 152104 | 6/2007 |
| JP | 2007 524461 | 8/2007 |
| JP | 2008 173236 | 7/2008 |
| JP | 2008-194456 A | 8/2008 |
| JP | 2009 82442 | 4/2009 |
| JP | 2009 195380 | 9/2009 |
| JP | 2010-29481 A | 2/2010 |

OTHER PUBLICATIONS

Office Action issued on Feb. 3, 2015 in Japanese Patent Application No. 2011-008632.

Combined Office Action and Search Report issued Nov. 24, 2014 in Chinese Patent Application No. 201280003819.2 (with English Translation of Category of Cited Documents).

* cited by examiner

MEDICAL IMAGE PROCESSING APPARATUS, AN X-RAY CT SCANNER, AND A MEDICAL IMAGE PROCESSING PROGRAM

FIELD OF THE INVENTION

An embodiment of the present invention relates to a medical image processing apparatus, an X-ray CT scanner, and a medical image processing program that calculates information used for evaluation of the differentiation of cancers based on medical images.

BACKGROUND OF THE INVENTION

Technologies have been developed for diagnosing whether pulmonary nodules are benign or malignant. For example, by observing the shape and size of probable pulmonary nodules over time using CT images obtained by means of an X-ray CT scanner, focused regions likely to turn malignant have been detected. However, in order to accurately identify them as cancer, diagnosis with combining results of functional tests by means of SPECT or PET has become necessary.

Moreover, perfusion tests using an X-ray CT scanner have been performed. Perfusion testing is a method of imaging a subject in which a contrast agent has been injected by means of an X-ray CT scanner and diagnosing based on imaging results.

PRIOR ART DOCUMENTS

Patent Document

[Patent Document 1] Japanese Unexamined Patent Application Publication No. 2009-195380

SUMMARY OF THE INVENTION

Problem to be Solved by the Invention

Conventionally, it was necessary to perform tests using two types of diagnostic apparatuses (for example, an X-ray CT scanner and SPECT) in order to identify probable pulmonary nodules as cancer. This resulted in inconvenience in hospitals.

Moreover, there are a plurality of parameters regarding morphological information of probable pulmonary nodules such as shape and size, making it necessary for physicians to determine the plurality of parameters using a complex approach for diagnosis. In order to improve the accuracy of diagnosis, it is necessary to supplement functional information, which is the result of the functional test, for diagnosis by physicians.

Physicians also need to determine the information obtained by means of perfusion testing from an X-ray CT scanner using a complex approach for diagnosis. In order to improve the accuracy of diagnosis, diagnosis by physicians is necessary after supplementing morphological information obtained from CT image data obtained under non-contrast conditions.

One problem to be solved by the present invention is to provide a medical image processing apparatus, an X-ray CT scanner, and a medical image processing program that can improve the accuracy of identifying the amount of characteristics of progression indicating the extent of probable disease.

Means for Solving the Problems

The medical image processing apparatus of the embodiment comprises a specifying means, a first computing means, a second computing means, and a third computing means. The specifying means specifies a probable disease from medical image data upon receiving the medical image data obtained by imaging a subject by means of a single medical imaging apparatus. The first computing means calculates morphological information indicating the characteristics of forms of the probable disease specified based on this medical image data. The second computing means calculates functional information of the specified probable disease based on this medical image data. The third computing means calculates the amount of characteristics of progression indicating the extent of probable disease based on the morphological information and functional information. In this context, one probable disease is a tumor or nodule.

The medical image processing program of the embodiment causes a computer to execute a specifying function, a first calculation function, a second calculation function, and a third calculation function. The specifying function is a function that specifies a probable disease from medical image data upon receiving the medical image data obtained by imaging a subject by means of a single medical imaging apparatus. The first calculation function is a function that calculates morphological information indicating the characteristics of forms of the specified probable disease based on this medical image data. The second calculation function is a function that calculates functional information of the specified probable disease based on this medical image data. The third calculation function is a function that calculates the amount of characteristics of progression indicating the extent of the probable disease based on the morphological information and the functional information.

MODE FOR CARRYING OUT THE INVENTION

Figure 1:
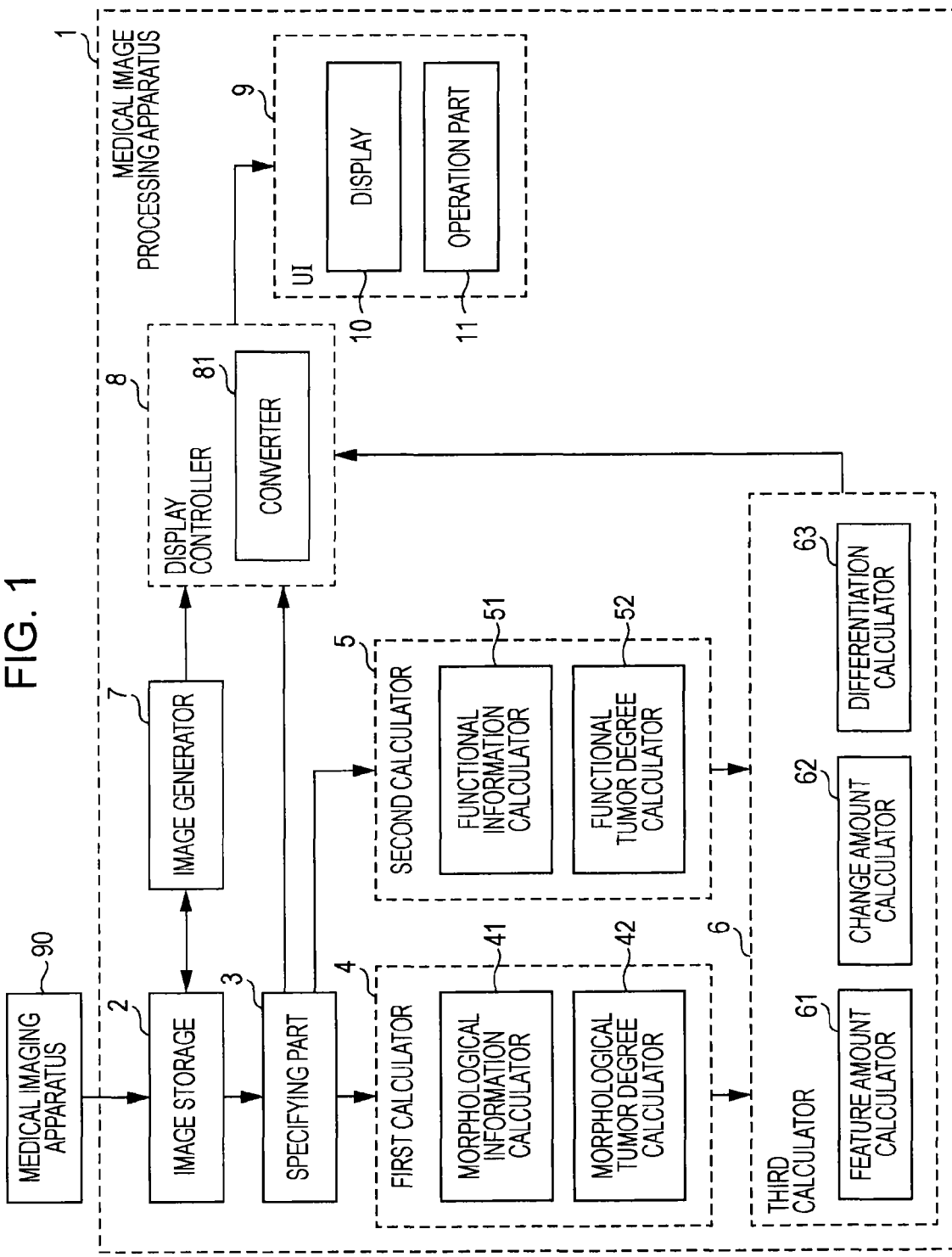
FIG. 1 is a block diagram showing the medical image processing apparatus according to the embodiment.

An explanation is provided regarding the medical image processing apparatus according to the embodiment with reference to FIG. 1. A medical image processing apparatus 1 according to the present embodiment is connected to a medical imaging apparatus 90.

(Medical Imaging Apparatus 90)

An example of the medical imaging apparatus 90 includes an X-ray CT scanner. The medical imaging apparatus 90 generates medical image data by imaging a subject. The medical imaging apparatus 90 outputs the medical image data to the medical image processing apparatus 1. An image storage 2 of the medical imaging apparatus 90 stores the medical image data.

The medical imaging apparatus 90 generates volume data, for example, by imaging a 3-dimensional region. Take the lungs as an example. In this case, by imaging the chest of the subject, the medical imaging apparatus 90 generates volume data of the chest.

Moreover, the medical imaging apparatus 90 generates a plurality of volume data (plurality of volume data imaged at different times respectively) in chronological order by continuously imaging the 3-dimensional region by setting the same region of the subject as the imaging object. If the lungs are imaged as the imaging object, the medical imaging apparatus 90 generates the plurality of volume data in chronological order by continuously imaging the chest. Cases are set forth below in which the lungs are the object.

The medical imaging apparatus 90 outputs the volume data of the chest to the medical image processing apparatus 1. The image storage 2 stores the volume data of the chest.

In the present embodiment, so-called contrast imaging (perfusion testing) is performed. That is, the medical imaging apparatus 90 generates a plurality of volume data in chronological order by continuously imaging the chest by setting the same region (for example, the lungs) of the subject in which the contrast agent has been injected as the imaging object. The volume data obtained after the contrast agent has been injected into the subject is referred to as "contrast volume data." The volume data obtained without the contrast agent being injected into the subject is referred to as "non-contrast volume data."

Figure 2:
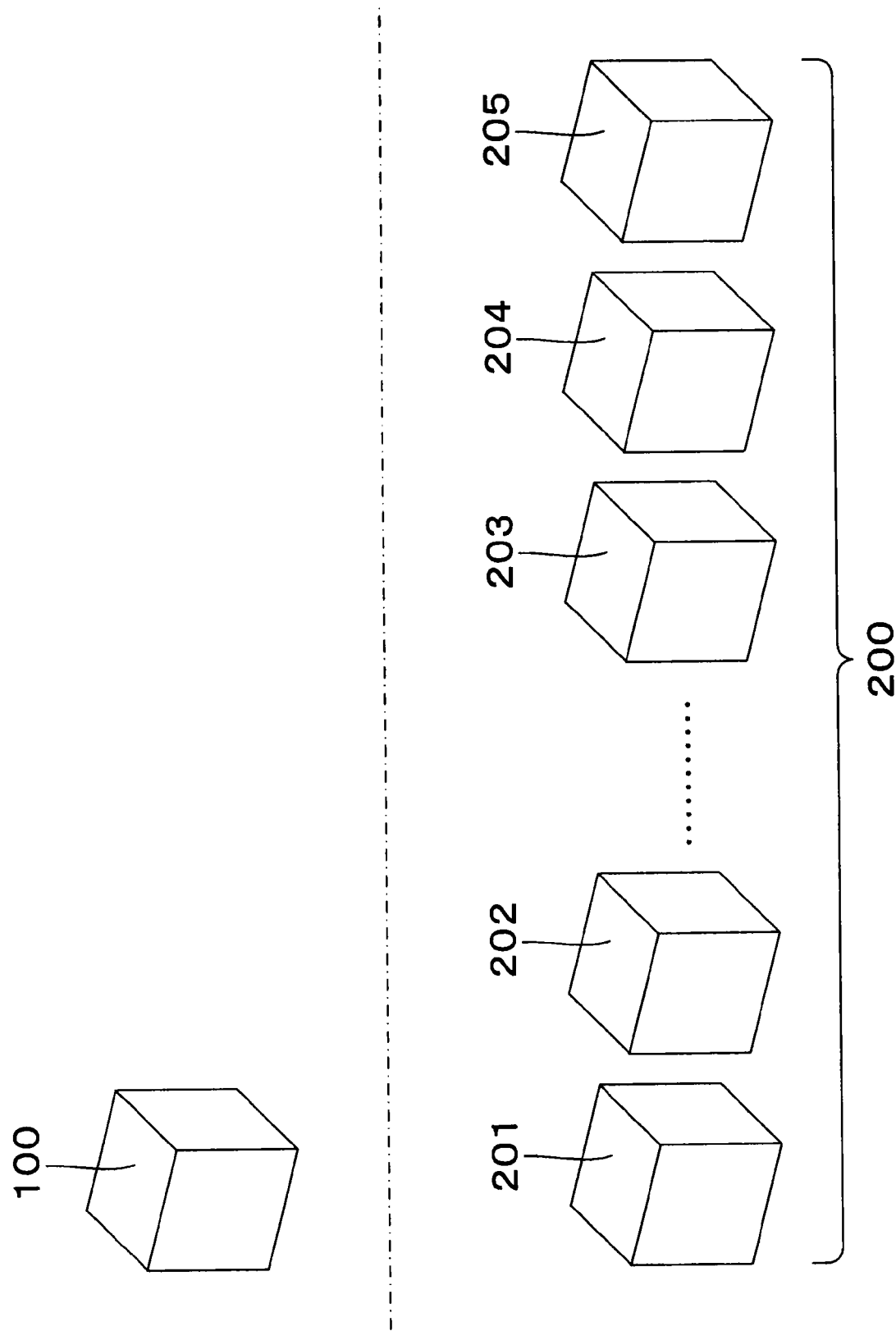
FIG. 2 is a diagram schematically showing the medical image data obtained in the embodiment.

The medical image data obtained in the present embodiment is shown in FIG. 2. FIG. 2 is a diagram schematically showing the medical image data obtained in the present embodiment in addition to the relationship between non-contrast volume data and the plurality of contrast volume data. With non-contrast imaging, the medical imaging apparatus 90 generates non-contrast volume data 100 of the chest. Moreover, with contrast imaging, the medical imaging apparatus 90 generates a contrast volume data group 200 containing the plurality of contrast volume data in chronological order. The contrast volume data group 200 includes the plurality of volume data such as contrast volume data 201, contrast volume data 202, contrast volume data 203, contrast volume data 204, and contrast volume data 205. The plurality of contrast volume data contained in the contrast volume data group 200 is data imaged at different times respectively. For example, the medical imaging apparatus 90 generates each contrast volume data in the order of the contrast volume data 201, the contrast volume data 202, . . . , and the contrast volume data 203. The image storage 2 stores the non-contrast volume data 100 and the contrast volume data group 200.

(Medical Image Processing Apparatus 1)

The medical image processing apparatus 1 comprises the image storage 2, a specifying part 3, a first calculator 4, a second calculator 5, a third calculator 6, an image generator 7, a display controller 8, and a user interface 9 (UI).

(Image Storage 2)

The image storage 2 stores the medical image data generated by means of the medical imaging apparatus 90. For example, the image storage 2 stores the non-contrast volume data of the chest. Moreover, the image storage 2 stores the plurality of contrast volume data in chronological order obtained by means of contrast imaging.

(Specifying Part 3)

The specifying part 3 reads the volume data from the image storage 2 and specifies from the volume data a probable pulmonary nodule (tumor) as a probable disease. For example, the specifying part 3 reads the non-contrast volume data 100 shown in FIG. 2 from the image storage 2 and specifies the probable pulmonary nodule based on the pixel value (CT value) of the non-contrast volume data 100. For example, the specifying part 3 specifies the range having a pixel value of more than the threshold calculated based on the experience as a probable pulmonary nodule. Moreover, the specifying part 3 may specify a probable pulmonary nodule among the plurality of contrast volume data obtained by means of contrast imaging, based on the volume data obtained in the time phase before the contrast agent flows in around the imaging object. For example, if the contrast volume data 201 shown in FIG. 2 is the volume data obtained in the time phase before the contrast agent flows in around the lungs, the specifying part 3 specifies the probable pulmonary nodule based on the contrast volume data 201. If the specifying part 3 specifies the probable pulmonary nodule based on the contrast volume data 201, the non-contrast volume data 100 may not have to be generated. That is, the medical imaging apparatus 90 may generate only the contrast volume data group 200 by performing contrast imaging alone without performing non-contrast imaging. The specifying part 3 outputs the location information (coordinate information) indicating the position of the probable pulmonary nodule (tumor) to the first calculator 4, the second calculator 5, and the display controller 8.

Figure 3:
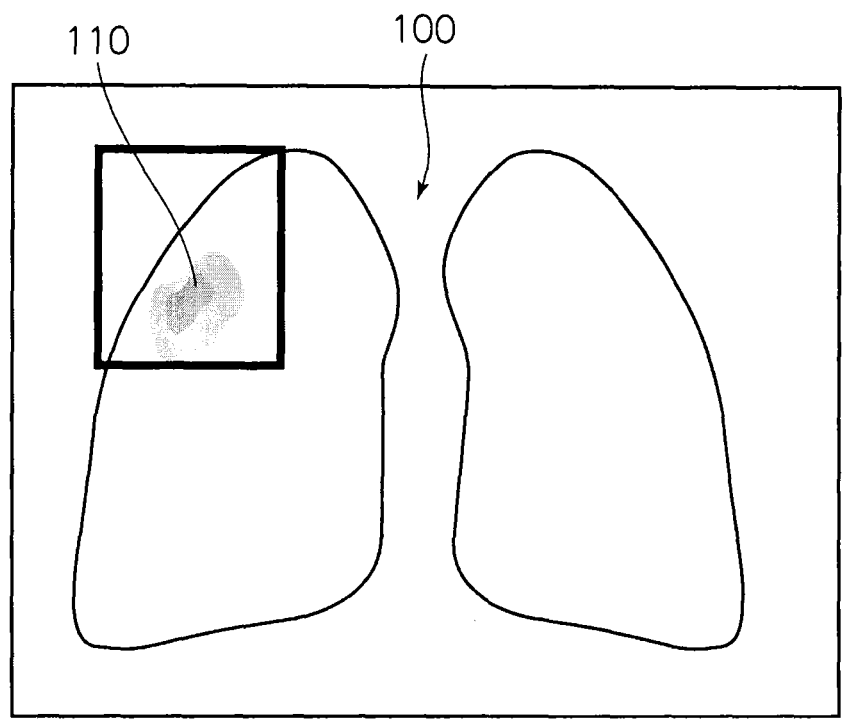
FIG. 3 is a diagram showing an image of the lungs for setting forth a region of probable pulmonary nodules.

An example of a probable pulmonary nodule specified as a probable disease specified by means of the specifying part 3 is shown in FIG. 3. FIG. 3 is a diagram showing an image of the lungs explaining the region of the probable pulmonary nodule. For example, the specifying part 3 specifies a probable pulmonary nodule 110 based on the pixel value (CT value) of the non-contrast volume data 100.

(First Calculator 4)

The first calculator 4 comprises a morphological information calculator 41 and a morphological tumor degree calculator 42.

(Morphological Information Calculator 41)

The morphological information calculator 41 calculates morphological information indicating the characteristics of the morphology of a probable pulmonary nodule (tumor) upon receiving the location information and volume data of the probable pulmonary nodule (tumor). For example, the morphological information calculator 41 calculates morphological information indicating the characteristics of the morphology of the probable pulmonary nodule based on the non-contrast volume data 100. Examples of morphological information include the size of the probable pulmonary nodule, the shape of the probable pulmonary nodule of the probable pulmonary nodule, the shape of unevenness of the surface of the probable disease, and the inner structure of the probable pulmonary nodule. The inner structure includes the state of a hollow formed on the inner side of the probable pulmonary nodule and uniformity of the pixel value (CT value) of the probable pulmonary nodule. An example of the state of a hollow includes the size of a hollow (area). The morphological information calculator 41 calculates at least one piece of information among the size of the probable pulmonary nodule, the shape of the probable pulmonary nodule, the shape of unevenness of the surface of the probable disease, and the hollow state of the probable pulmonary nodule, as morphological information. That is, the morphological information calculator 41 may calculate the plurality of information or only one piece of information regarding the probable pulmonary nodule, among the size, the shape, the shape of unevenness of the surface, the hollow state, and the uniformity of the pixel value. For example, an operator may specify the types of morphological information calculated by means of the morphological information calculator 41 using an operation part 13. In this case, the morphological information calculator 41 calculates the morphological information specified by the operator.

The morphological information calculator 41 calculates the area of the probable pulmonary nodule as an example of the size of the probable pulmonary nodule. The morphological information calculator 41 specifies the shape of the probable pulmonary nodule and categorizes the specified shape into any one of spherical, triangular, linear, oval, or irregular shapes. For example, the morphological information calculator 41 categorizes the shape of the probable pulmonary nodule by means of pattern matching. The morphological information calculator 41 calculates the shape of unevenness of the surface of the probable pulmonary nodule and categorizes the shape of unevenness into any one of spicular, smooth, or lobulated shapes. For example, the morphological information calculator 41 categorizes the shape of unevenness by means of pattern matching. The morphological information calculator 41 calculates the area of the hollow formed on the inner side of the probable pulmonary nodule as an example of the hollow state. The morphological information calculator 41 calculates variations in the pixel value (CT value) of a plurality of pixel elements inside the probable pulmonary nodule, as an example of the uniformity of the pixel value (CT value).

(Morphological Tumor Degree Calculator 42)

The morphological tumor degree calculator 42 calculates the tumor degree (the amount of characteristics) (may also be referred to as the progression of the disease) indicating the extent of the tumor with respect to the morphology of the probable pulmonary nodule (tumor) based on the morphological information. The tumor degree (the amount of characteristics) calculated by means of the morphological information is referred to as the "morphological tumor degree" (morphological characteristics amount). The morphological tumor degree calculator 42 scores the morphological information and calculates the morphological tumor degree based on this score. For example, a score table in which the morphological information and the scores are associated with each other is created in advance and stored in advance in the storage (not shown in the figures). The morphological tumor degree calculator 42 calculates the scores corresponding to the morphological information with reference to the score table. The scores are standardized values based on malignant tissues. As an example, the morphological tumor degree calculator 42 sets the score of malignant tissues as "10," and conducts scoring according to the size of the value indicated by the morphological information based on the score of the malignant tissues.

If the size of the probable pulmonary nodule is calculated, the morphological tumor degree calculator 42 scores the size of the probable pulmonary nodule. For example, a score table is stored in advance in which the size of the probable pulmonary nodule and the score are associated with each other in storage (not shown in the figures). The larger the size of the probable pulmonary nodule, the higher the tumor degree is presumed to be (the extent of the tumor); therefore, the larger the probable pulmonary nodule, the higher the score. The morphological tumor degree calculator 42 calculates the score corresponding to the size of the probable pulmonary nodule with reference to the score table.

If the shape of the probable pulmonary nodule is determined and the shapes are categorized, the morphological tumor degree calculator 42 scores the shape of the probable pulmonary nodule. For example, it stores in advance a score table in which the shape of the probable pulmonary nodule and the score are associated with each other in storage (not shown in the figures). Specifically, a score table is stored in advance in which each of spherical, triangular, linear, oval, and irregular shapes and the scores are associated with each other in storage (not shown in the figures). It is presumed that the tumor degree (the extent of the tumor) varies depending on the shape of the probable pulmonary nodule; therefore, classification of the shape of the probable pulmonary nodule and the scores are associated with each other. The morphological tumor degree calculator 42 calculates the scores corresponding to the classification of the shape of the probable pulmonary nodule with reference to the score table.

If the shape of unevenness of the surface of the probable pulmonary nodule is categorized, the morphological tumor degree calculator 42 scores the shape of unevenness. For example, it stores in advance a score table in which the shape of unevenness and the score are associated with each other in storage (not shown in the figures). Specifically, it stores in advance a score table in which each of spicular, smooth, and lobulated shapes and the scores are associated with each other in storage (not shown in the figures). It is presumed that the tumor degree (the extent of tumor) varies depending on the shape of unevenness of the surface; therefore, classification of the shape of unevenness and the scores are associated with each other. The morphological tumor degree calculator 42 calculates the scores corresponding to the classification of the shape of unevenness with reference to the score table.

If the state of the hollow formed on the inner side of the probable pulmonary nodule is determined, the morphological tumor degree calculator 42 scores the hollow state. For example, it stores in advance a score table in which the size of the hollow and the scores are associated with each other in storage (not shown in the figures). It is presumed that the larger the hollow, the higher the tumor degree (extent of tumor); therefore, the larger the hollow, the higher the score. The morphological tumor degree calculator 42 calculates the scores corresponding to the size of the hollow with reference to the score table.

If the uniformity of the pixel value (CT value) of the probable pulmonary nodule is calculated, the morphological tumor degree calculator 42 scores the uniformity of the pixel value. For example, it stores in advance a score table in which the uniformity of the pixel value and the scores are associated with each other in storage (not shown in the figures). It is presumed that the larger the extent of variations in the pixel value, the higher the tumor degree (extent of tumor); therefore, the larger the variation in the pixel value, the higher the score. The morphological tumor degree calculator 42 calculates the scores corresponding to the uniformity (variation) of the pixel value with reference to the score table.

The morphological tumor degree calculator 42 calculates the morphological tumor degree based on the scores of the morphological information. For example, the morphological tumor degree calculator 42 calculates the morphological tumor degree based on the scores of at least one piece of information among the size of the probable pulmonary nodule, the shape of the probable pulmonary nodule, the shape of unevenness of the surface of the probable pulmonary nodule, the state of the hollow of the probable pulmonary nodule, and the uniformity of the pixel value (CT value).

The combination of the scores of the above morphological information is just an example, and it may combine the scores of any piece of the morphological information and calculate the morphological tumor degree. Moreover, the scores of one piece of the morphological information may be set as the morphological tumor degree. The operator may specify the types of the morphological tumor degree calculated by means of the morphological tumor degree calculator 42, using an operation part 11. In this case, the morphological tumor degree calculator 42 calculates the morphological tumor degree specified by the operator.

Instead of the morphological tumor degree calculator 42 calculating the score of the morphological information, the operator may provide a score. For example, the image generator 7 reads the non-contrast volume data from the image storage 2 and generates MPR image data (image data on any cross section) based on the non-contrast volume data. The display controller 8 causes a display 10 to display the MPR image based on the MPR image data. The operator refers to the MPR image displayed on the display 10 and scores with respect to at lease one piece of information among the size, the shape, the shape of unevenness, the hollow state, and the uniformity of the pixel value of the probable pulmonary nodule represented by the MPR image. The operator inputs the score using the operation part 11. The morphological tumor degree calculator 42 calculates the morphological tumor degree based on the score input by the operation part 11. In this way, the operator may score the amount of morphological characteristics.

(Second Calculator 5)

The second calculator 5 comprises a functional information calculator 51 and a functional tumor degree calculator 52.

(Functional Information Calculator 51)

The functional information calculator 51 calculates functional information indicating the hemodynamics in the probable pulmonary nodule (tumor) upon receiving the location information and volume data of the probable pulmonary nodule (tumor). The functional information calculator 51 calculates functional information indicating the hemodynamics, etc., of the probable pulmonary nodule based on the contrast volume data group 200 containing the plurality of contrast volume data in chronological order. Examples of the functional information include the degree of elevation of the pixel values (CT value) of the probable pulmonary nodule, the blood flow of the probable pulmonary nodule, the distribution volume (blood volume) of the probable pulmonary nodule, the transit time of the blood of the probable pulmonary nodule, and the ratio of the blood flow of the probable pulmonary nodule. Moreover, other than the hemodynamics, the functional information can also include elasticity and the degree of deformation (including movement as well).

Figure 5:
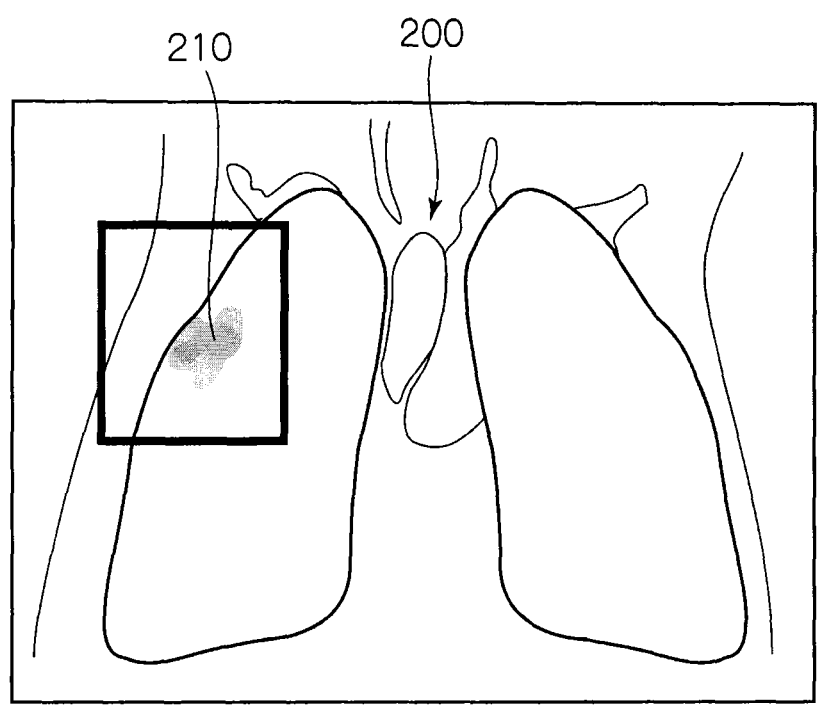
FIG. 5 is a diagram showing an image of the lungs for setting forth the processing that calculates functional information.

The contrast volume data group 200 is the volume data obtained in the state in which the contrast agent is injected into the subject. An example of the image obtained in the state in which the contrast agent is injected into the subject is shown in FIG. 5. FIG. 5 is a diagram showing an image of the lungs for explaining the processing that calculates the functional information. The contrast agent injected into the subject flows into a probable pulmonary nodule 210 or tissues around the lungs and flows out with time. In this way, the amount of the contrast agent changes with time and the pixel value (CT value) of the contrast volume data group 200 changes according to the amount of the contrast agent. The functional information calculator 51 calculates the functional information of the probable pulmonary nodule 210 based on the pixel value of the contrast volume data group 200.

The functional information calculator 51 calculates at least one piece of information among the degree of elevation of the pixel value, the blood flow, the distribution volume (blood volume), the transit time, and the ratio of the blood flow as functional information. That is, the functional information calculator 51 may calculate the plurality of information or one piece of information among the degree of elevation of the pixel value, the blood flow, the distribution volume (blood volume), the transit time, and the ratio of the blood flow. For example, the operator may specify the types of functional information calculated by means of the functional information calculator 51 using the operation part 13. In this case, the functional information calculator 51 calculates the functional information specified by the operator.

As an example of the degree of elevation of the pixel value (CT value) of the probable pulmonary nodule, the functional information calculator 51 calculates the degree of elevation of the pixel value per unit time of the probable pulmonary nodule. As an example of the blood flow of the probable pulmonary nodule, the functional information calculator 51 calculates the blood flow per unit volume and unit time of the probable pulmonary nodule. As an example of the distribution volume (blood volume) of the probable pulmonary nodule, the functional information calculator 51 calculates the distribution volume (blood volume) per unit volume inside the probable pulmonary nodule. As an example of the transit time of the blood of the probable pulmonary nodule, the functional information calculator 51 calculates the average transit time of the blood of the probable pulmonary nodule. As an example of the ratio of the blood flow of the probable pulmonary nodule, the functional information calculator 51 calculates the ratio of the blood flow of the probable pulmonary nodule with respect to the blood flow of the surrounding region of the probable pulmonary nodule.

(Functional Tumor Degree Calculator 52)

The functional tumor degree calculator 52 calculates the tumor degree (the amount of characteristics) indicating the extent of the tumor with respect to the hemodynamics of the probable pulmonary nodule (tumor), based on the functional information. The tumor degree (the amount of characteristics) calculated by means of the functional information shall be referred to as the "functional tumor degree (the amount of functional characteristics)." The functional tumor degree calculator 52 scores the functional information and calculates the functional tumor degree based on this score. For example, a score table in which the functional information and the score are associated with each other is created in advance and is stored in advance in storage (not shown in the figures). The functional tumor degree calculator 52 calculates the score corresponding to the functional information with reference to the score table. The scores are standardized values based on, for example, malignant tissues. As an example, the functional tumor degree calculator 52 sets the score of malignant tissues as "10," and scores the association with the malignant alteration degree shown by the functional information based on the score of malignant tissues.

If a plurality of parameters (indices) are scored respectively, the scores are weighed according to the contribution level of detection of malignant alteration (detection accuracy) of each parameter. Note that the amount of functional characteristics may include the amount of progress characteristics indicating the extent of the probable disease; however, an explanation is provided here using the amount of malignant characteristics.

If the elevation of the pixel value (CT value) of the probable pulmonary nodule is calculated, the functional tumor degree calculator 52 scores the elevation of the pixel value. For example, it stores in advance a score table in which the elevation of the pixel value and the score are associated with each other in storage (not shown in the figures). It is presumed that the higher the degree of elevation of the pixel value of the probable pulmonary nodule, the higher the tumor degree (the extent of the tumor); therefore, the higher the degree of elevation of the pixel value, the higher the score. The functional tumor degree calculator 52 calculates a score corresponding to the degree of elevation of the pixel value with reference to the score table.

If the blood flow of the probable pulmonary nodule is calculated, the functional tumor degree calculator 52 scores the blood flow. For example, it stores in advance a score table in which the blood flow of the probable pulmonary nodule and the score are associated with each other in storage (not shown in the figures). It is presumed that the greater the blood flow in the probable pulmonary nodule, the higher the tumor degree (the extent of the tumor); therefore, the greater the blood flow, the higher the score. The functional tumor degree calculator 52 calculates the score corresponding to the blood flow with reference to the score table.

If the distribution volume (blood volume) of the probable pulmonary nodule is calculated, the functional tumor degree calculator 52 scores the distribution volume (blood volume). For example, it stores in advance a score table in which the distribution volume (blood volume) of the probable pulmonary nodule and the score are associated with each other in storage (not shown in the figures). It is presumed that the greater the distribution volume (blood volume) in the probable pulmonary nodule, the higher the tumor degree (the extent of the tumor); therefore, the greater the distribution volume (blood volume), the higher the score. The functional tumor degree calculator 52 calculates the score corresponding to the distribution volume (blood volume) with reference to the score table.

If the transit time of the blood in the probable pulmonary nodule is calculated, the functional tumor degree calculator 52 scores the transit time of the blood. For example, it stores in advance a score table in which the transit time of the blood in the probable pulmonary nodule and the score are associated with each other in storage (not shown in the figures). It is presumed that the longer the transit time of the blood, the higher the tumor degree (extent of the tumor); therefore, the longer the transit time, the higher the score. The functional tumor degree calculator 52 calculates the score corresponding to the transit time with reference to the score table.

If the ratio of the blood flow in the probable pulmonary nodule is calculated, the functional tumor degree calculator 52 scores the ratio of the blood flow. For example, it stores in advance a score table in which the ratio of the blood flow in the probable pulmonary nodule and the score are associated with each other in storage (not shown in the figures). It is presumed that the larger the ratio of the blood flow, the higher the tumor degree (the extent of the tumor); therefore, the larger the ratio of the blood flow, the higher the score. The functional tumor degree calculator 52 calculates the score corresponding to the ratio of the blood flow with reference to the score table.

The functional tumor degree calculator 52 calculates the functional tumor degree based on the score of the functional information. For example, the functional tumor degree calculator 52 calculates the functional tumor degree based on the score of at least one piece of information among the degree of elevation of the pixel value (CT value) of the probable pulmonary nodule, the blood flow of the probable pulmonary nodule, the distribution volume (blood volume) of the probable pulmonary nodule, the transit time of the blood in the probable pulmonary nodule, and the ratio of the blood flow in the probable pulmonary nodule.

Figure 6:
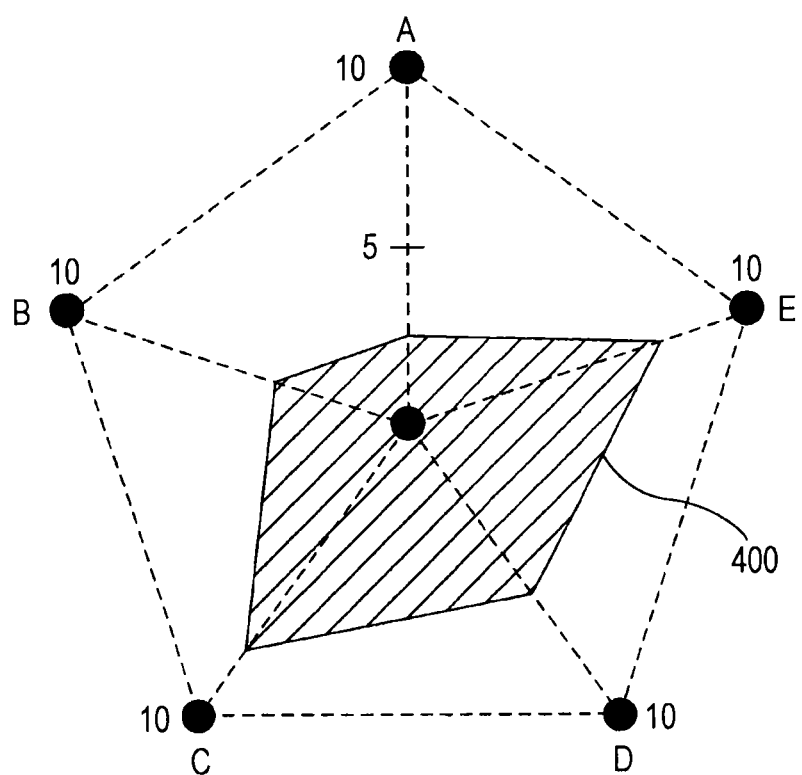
FIG. 6 is a radar chart showing the relationship between functional information and functional tumor degree.

As an example, an explanation is provided for cases in which the scores are calculated for the degree of elevation of the pixel value, the blood flow, the distribution volume (blood volume), the transit time of the blood, and the ratio of the blood flow, respectively. For example, the functional tumor degree calculator 52 expresses the scores of the respective functional information on a graph and calculates the functional tumor degree based on this graph. An explanation is provided regarding the relationship between the functional information and the functional tumor degree with reference to FIG. 6. FIG. 6 is a radar chart showing the relationship between the functional information and the functional tumor degree. As an example, as shown in FIG. 6, the functional tumor degree calculator 52 creates a pentagon-shaped radar chart (graph) having the scores of five types of functional information as respective variables. The functional tumor degree calculator 52 plots the scores (standardized values) of each piece of functional information on the radar chart and connects the dots of the scores located next to each other. The functional tumor degree calculator 52 calculates the area of a range 400 (the range shown by diagonal lines) in which the dots of the scores located next to each other have been connected. The area of the range 400 is equivalent to the functional tumor degree. The functional tumor degree calculator 52 outputs the information indicating the functional tumor degree (for example, the area of the range 400) to the third calculator 6.

As another example, the functional tumor degree calculator 52 may calculate the functional tumor degree based on the scores of each of the blood flow, the distribution volume (blood volume), and the ratio of the blood flow. In this case, the functional tumor degree calculator 52 creates a triangular radar chart with the scores of three types of functional information as variables. The functional tumor degree calculator 52 plots the scores of the respective functional information on the radar chart and connects the dots of the scores located next to each other. The functional tumor degree calculator 52 calculates the area of the range in which the dots of the scores located next to each other have been connected, as the functional tumor degree. The state of the tumor is easily reflected in the blood flow, the distribution volume (blood volume), and the ratio of the blood flow. Therefore, a functional tumor degree reflecting the state of the tumor as being in a good condition is obtained using the scores regarding the blood flow, distribution volume (blood volume), and the ratio of the blood flow.

The combination of the scores of the above functional information is just an example; in fact, the functional tumor degree may be calculated by combining the scores of any pieces of functional information. Moreover, the score of one piece of functional information may be set as the functional tumor degree. The operator may specify types of the functional tumor degree calculated by means of the functional tumor degree calculator 52 using the operation part 11. In this case, the functional tumor degree calculator 52 calculates the functional tumor degree specified by the operator.

(Third Calculator 6)

The third calculator 6 comprises a feature amount calculator 61, a change amount calculator 62, and a differentiation calculator 63.

(Feature Amount Calculator 61)

The feature amount calculator 61 receives information indicating the morphological tumor degree from the morphological tumor degree calculator 42 and receives information indicating the functional tumor degree from the functional tumor degree calculator 52. The feature amount calculator 61 calculates the nodule characteristics score (the amount of malignant characteristics) indicating the extent of the tumor of the probable pulmonary nodule based on the morphological tumor degree and the functional tumor degree. For example, it creates in advance a score table in which the morphological tumor degree, the functional tumor degree, and the nodule characteristics scores are associated and stores it in advance in storage (not shown in the figures). The feature amount calculator 61 calculates the nodule characteristics score corresponding to the morphological tumor degree and the functional tumor degree with reference to the score table.

As an example, the feature amount calculator 61 calculates the nodule characteristics score (the amount of malignant characteristics) based on the area of a range 300 equivalent to the morphological tumor degree and the area of the range 400 equivalent to the functional tumor degree. For example, it stores in advance a score table in which the area of the range 300 equivalent to the morphological tumor degree, the area of the range 400 equivalent to the functional tumor degree, and the nodule characteristics score (the amount of malignant characteristics) have been associated with each other in storage (not shown in the figures). The higher the morphological tumor degree, the higher the nodule characteristics score, and the higher the functional tumor degree, the higher the nodule characteristics score. The feature amount calculator 61 calculates the nodule characteristics score corresponding to the area equivalent to the morphological tumor degree and the area corresponding to the functional tumor degree with reference to the score table. The feature amount calculator 61 outputs information indicating the nodule characteristics score (the amount of malignant characteristics) to the display controller 8.

Figure 7:
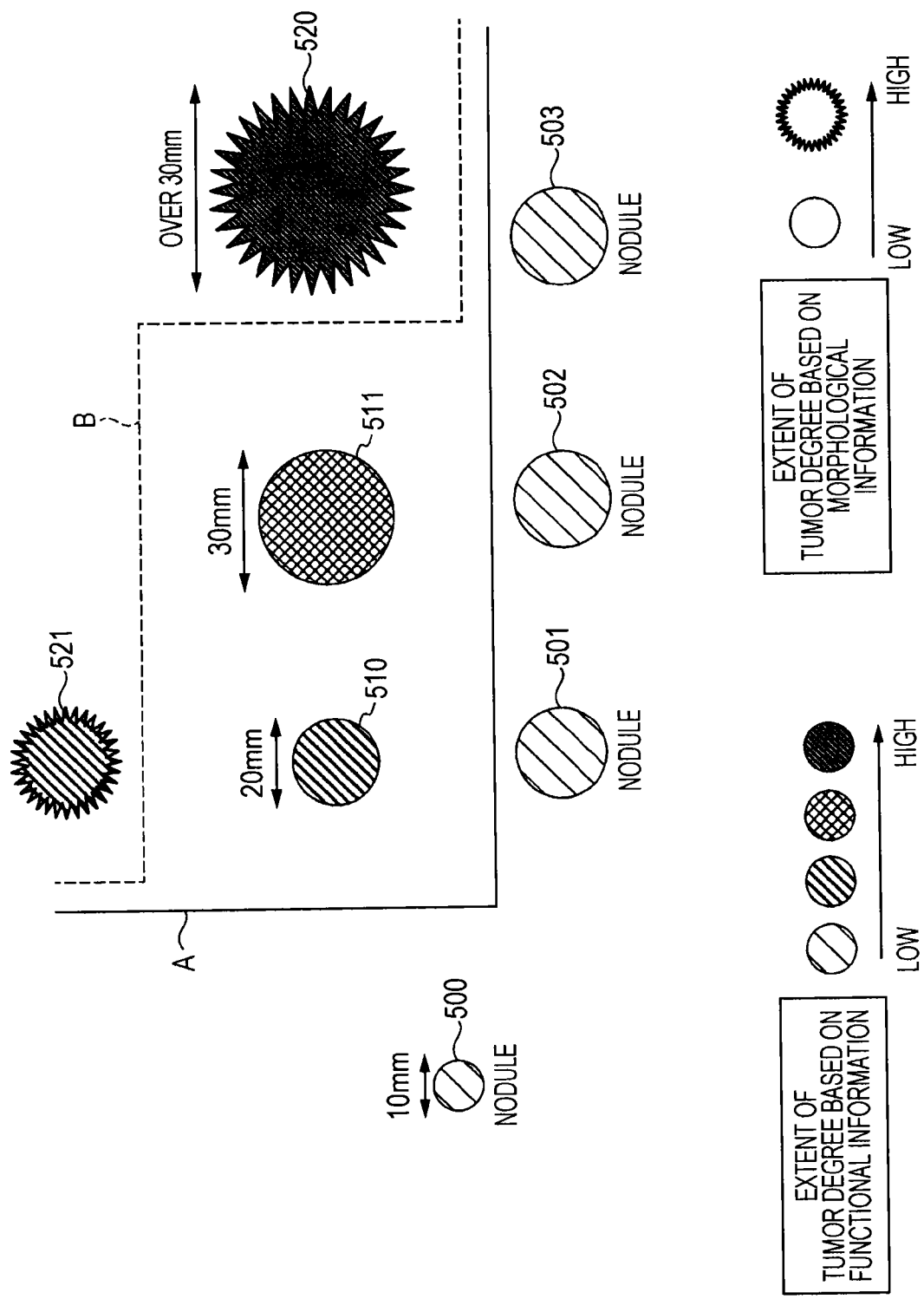
FIG. 7 is a diagram schematically showing the extent of disease progression (nodule characteristics score).

The relationship between the morphological tumor degree, the functional tumor degree, and the nodule characteristics score is shown in FIG. 7. FIG. 7 is a diagram schematically indicating the extent of the tumor (nodule characteristics score). A nodule model 500, etc., shows the extent of the tumor degree (morphological tumor degree) based on the morphological information and the extent of the tumor degree (functional tumor degree) based on the functional information. The shape and size of each nodule model indicate the extent of the tumor degree (morphological tumor degree) based on the morphological information. The types of hatching inside each nodule model indicate the extent of the tumor degree (functional tumor degree) based on the functional information. For example, the nodule model 500, the nodule model 501, the nodule model 502, and the nodule model 503 indicate that the functional tumor degree is low and that it is less likely to turn malignant in the current state. As an example, the diameter of the nodule model 500 is 10 mm and the extent of the functional tumor degree is also low; thereby, indicating that it is less likely to be malignant in the current state. Regarding the nodule model 510 and the nodule model 511, the size is comparatively large and the functional tumor degree is also relatively high, indicating that it is likely to be malignant. For the nodule model 520 and the nodule model 521, the size is large, unevenness of the surface is pointed, and the degree of the functional tumor degree is also high, indicating that they have become malignant.

The solid line A indicates the boundary of detection accuracy by means of the medical image processing apparatus 1 according to the present embodiment. The dashed line B indicates the boundary of detection accuracy by means of a method according to conventional technology. For identifying malignancy based on the morphological information only as per conventional technology, it is possible to detect the degree of the tumor equivalent to the nodule model 520 and the nodule model 521; however, it is not possible to detect the degree of the tumor equivalent to the nodule model 510 and the nodule model 511. That is, according to conventional technology, it is possible to detect a nodule that has already become malignant indicated by the nodule model 520 and the nodule model 521; however, it is not possible to detect a nodule which has a possibility of becoming malignant as indicated by the nodule model 510 and the nodule model 511. In this way, based on the morphological information only, it is difficult to detect a nodule which has a possibility of becoming malignant as shown by the nodule model 510 and the nodule model 511.

In contrast, the medical image processing apparatus 1 according to the present embodiment allows a nodule, which is difficult to be identified as malignant only from the morphological information, to be detected by identifying malignancy based on the morphological tumor degree and the functional tumor degree. The medical image processing apparatus 1 according to the present embodiment, for example, allows a nodule, which has a possibility of being malignant as shown by the nodule model 510 and the nodule model 511, to be detected. In this way, malignant transformation including the functional information is identified, making it possible to detect the nodule in the state in which it is difficult to be detected from the morphological information alone.

(Change Amount Calculator 62)

The change amount calculator 62 calculates the variation over time in the morphological tumor degree (the amount of morphological characteristics) respectively obtained by different imaging. Moreover, the change amount calculator 62 calculates the variation over time in the functional tumor degree (the amount of functional characteristics) respectively obtained by different imaging. For example, the same site of the subject is imaged for different times by means of the medical imaging apparatus 90 (first imaging and second imaging). The change amount calculator 62 obtains the variation in the morphological tumor degree over time by calculating the difference between the morphological tumor degree obtained by means of the first imaging and the morphological tumor degree obtained by means of the second imaging. The change amount calculator 62 obtains the variation in the functional tumor degree over time by calculating the difference between the functional tumor degree obtained by means of the first imaging and the functional tumor degree obtained by means of the second imaging.

Specifically, the medical imaging apparatus 90 carries out the first imaging to generate a plurality of volume data containing the non-contrast volume data and the contrast volume data. The image storage 2 stores the plurality of volume data obtained by means of the first imaging. As above, the specifying part 3 specifies the probable pulmonary nodule (tumor), using volume data obtained by means of the first imaging. The first calculator 4 calculates the morphological information and the morphological tumor degree, using the volume data obtained by means of the first imaging. The second calculator 5 calculates the morphological information and the morphological tumor degree, using the volume data obtained by means of the first imaging. The feature amount calculator 61 calculates the nodule characteristics score (the amount of malignant characteristics) based on the morphological tumor degree and the functional tumor degree. Data regarding the first imaging is stored in the image storage 2 as past data. That is, the image storage 2 stores the morphological information, the morphological tumor degree, the functional information, the functional tumor degree, and the nodule characteristics score obtained by means of the first imaging as past data.

Moreover, the medical imaging apparatus 90 carries out the second imaging, which is different from the first imaging, to generate the plurality of volume data containing the non-contrast volume data and the contrast volume data. For example, in order to test the progression of the tumor, the second imaging is performed after time elapses from when the first imaging is performed. The image storage 2 stores the plurality of volume data obtained by means of the second imaging. As above, the specifying part 3 specifies the probable pulmonary nodule (tumor, equivalent to one example of the second probable tumor), using the volume data obtained by means of the second imaging. The first calculator 4 calculates the morphological information (equivalent to one example of the second morphological information) and the morphological tumor degree (equivalent to one example of the second morphological tumor degree), using the volume data obtained by means of the second imaging. The second calculator 5 calculates the functional information (equivalent to one example of the second functional information) and the functional tumor degree (equivalent to one example of the second functional tumor degree), using the volume data obtained by means of the second imaging. The feature amount calculator 61 calculates the nodule characteristics score (the amount of malignant characteristics) based on the morphological tumor degree and the functional tumor degree. The image storage 2 stores data regarding the second imaging. That is, the image storage 2 stores morphological information, the morphological tumor degree, the functional information, the functional tumor degree, and the nodule characteristics score obtained by means of the second imaging.

The change amount calculator 62 reads the morphological tumor degree obtained by means of the first imaging (past imaging) and the morphological tumor degree obtained by means of the second imaging from the image storage 2 and calculates the difference in the morphological tumor degree, to determine variations over time in the morphological tumor degree. The change amount calculator 62 may read the functional tumor degree obtained by means of the first imaging and the functional tumor degree obtained by means of the second imaging from the image storage 2 and calculates the difference in the functional tumor degree, to determine variations in the functional tumor degree over time.

The change amount calculator 62 may obtain variations in the morphological information over time by calculating the difference between the morphological information obtained by means of the first imaging (past imaging) and the morphological information obtained by means of the second imaging. Moreover, the change amount calculator 62 may calculate variations in the functional information over time by calculating the difference between the functional information obtained by means of the first imaging and the functional information obtained by means of the second imaging. That is, the change amount calculator 62 may obtain variations in the same type of morphological information over time for the first imaging and the second imaging. Similarly, the change amount calculator 62 may calculate variations in the same type of functional information over time for the first imaging and the second imaging.

The change amount calculator 62 may calculate variations in the nodule characteristics score over time by calculating the difference between the nodule characteristics score obtained by means of the first imaging (past imaging) and the nodule characteristics score obtained by means of the second imaging.

The change amount calculator 62 outputs information indicating variations to the image storage 2 and the display controller 8. The image storage 2 stores the variations calculated by the change amount calculator 62. For example, the change amount calculator 62 outputs information indicating variations in the morphological tumor degree over time and information indicating variations in the functional tumor degree over time to the image storage 2 and the display controller 8. The image storage 2 stores information indicating variations in the morphological tumor degree over time and variations in the functional tumor degree over time.

(Differentiation Calculator 63)

The differentiation calculator 63 calculates the differentiation of the probable pulmonary nodule (tumor) based on the nodule characteristics score (the amount of malignant characteristics), variations in the morphological tumor degree over time, and variations in the functional tumor degree over time. For example, differentiation table is created associating the nodule characteristics score, variations in the morphological tumor degree over time, and variations in the functional tumor degree over time with each other and is stored in advance in storage (not shown in the figures). It is presumed that the larger the nodule characteristics score (the amount of malignant characteristics), variations in the morphological tumor degree over time, and variations in the functional tumor degree over time, the higher the differentiation of the tumor; therefore, the larger the nodule characteristics score (the amount of malignant characteristics), variations in the morphological tumor degree over time, and variations in the functional tumor degree over time, the higher the differentiation. The differentiation calculator 63 calculates the differentiation corresponding to the nodule characteristics score, the variations in the morphological tumor degree over time, and the variations in the functional tumor degree over time, with reference to the differentiation table. The differentiation calculator 63 outputs information indicating the differentiation to the display controller 8.

(Image Generator 7)

The image generator 7 creates 3-dimensional image data by reading the volume data from the image storage 2 and performing volume rendering on the volume data. The image generator 7 may create MPR image data (image data on any cross section) by performing MPR (Multi Planar Reconstruction) on the volume data. For example, the image generator 7 reads the non-contrast volume data from the image storage 2 and creates image data such as the 3-dimensional image data and the MPR image data based on the non-contrast volume data. The image generator 7 outputs image data such as the 3-dimensional image data and the MPR image data to the display controller 8.

(Display Controller 8)

The display controller 8 comprises a converter 81. The display controller 8 causes the display 10 to display images based on the image data upon receiving image data such as the 3-dimensional image data and the MPR image data from the image generator 7. For example, the display controller 8 causes the display 10 to display 3-dimensional images based on the 3-dimensional image data upon receiving the 3-dimensional image data generated based on the non-contrast volume data from the image generator 7. The display controller 8 causes the display 10 to display MPR images based on the MPR image data upon receiving the MPR image data generated based on the non-contrast volume data from the image generator 7.

(Converter 81)

The converter 81 converts the value of the nodule characteristics score into a color corresponding to the value, upon receiving information indicating the nodule characteristics score (the amount of malignant characteristics) from the feature amount calculator 61. For example, it changes the color according to the size of the nodule characteristics score, creates a color table in which the nodule characteristics score and the color are associated with each other, and stores it in advance in storage (not shown in the figures). The converter 81 converts the value of the nodule characteristics score into a color, with reference to the color table.

The converter 81 may convert variations in the morphological tumor degree over time into a color corresponding to the variations, upon receiving information indicating variations in the morphological tumor degree over time from the change amount calculator 62. For example, it changes color corresponding to variations in the morphological tumor degree over time, creates a color table in which the variations in the morphological tumor degree over time and color are associated with each other, and stores it in advance in storage (not shown in the figures). The converter 81 converts the variations in the morphological tumor degree over time with reference to the color table. Moreover, the converter 81 may convert the variations in the functional tumor degree over time to a color corresponding to the variations, upon receiving information indicating variations in the functional tumor degree over time from the change amount calculator 62. For example, it changes the color according to the variations in the functional tumor degree over time, creates a color table in which the variations in the functional tumor degree over time and the color are associated with each other, and stores it in advance in storage (not shown in the figures). The converter 81 converts variations in the functional tumor degree over time into a color, with reference to the color table.

The converter 81 may convert the differentiation into a color corresponding to the differentiation, upon receiving information indicating differentiation from the differentiation calculator 63. For example, it changes color corresponding to the differentiation, creates a color table in which the differentiation and color are associated with each other, and stores it in advance in storage (not shown in the figures). The converter 81 converts the differentiation into a color, with reference to the color table.

The display controller 8 receives the location information indicating the location of the probable pulmonary nodule (tumor) from the specifying part 3. Upon applying a color corresponding to the nodule characteristics score at the position of the probable pulmonary nodule above the image, the display controller 8 causes the display 10 to display the image. For example, upon receiving the MPR image data generated based on the non-contrast volume data, the display controller 8 applies a color corresponding to the nodule characteristics score at the position of the probable pulmonary nodule above the MPR image, to cause the display 10 to display the MPR image.

The display controller 8 may apply a color corresponding to the differentiation at the position of the probable pulmonary nodule above the image to cause the display 10 to display the image. The display controller 8 may apply a color corresponding to variations in the morphological tumor degree over time at the position of the probable pulmonary nodule above the image to cause the display 10 to display the image. The display controller 8 may apply a color corresponding to variations in the functional tumor degree over time at the position of the probable pulmonary nodule above the image to cause the display 10 to display the image.

(User Interface (UI) 9)

The user interface (UI) 9 comprises the display 10 and the operation part 11. The display 10 includes a monitor such as a CRT and a liquid-crystal display. The operation part 11 comprises an input device such as a keyboard and a mouse.

The specifying part 3, the first calculator 4, the second calculator 5, the third calculator 6, the image generator 7, and the display controller 8 may be comprised from a processing apparatus such as a CPU, a GPU, or an ASIC (not shown in the figures) and a storing device such as a ROM, a RAM, or a HDD (not shown in the figures), respectively. Stored in the storing device is a specific program for executing a function of the specifying part 3. Moreover, stored in the storing device is a first computing program for executing a function of the first calculator 4. Stored in the first computing program are a morphological information computing program for executing a function of the morphological information calculator 41 and a morphological tumor degree calculation program for executing a function of the morphological tumor degree calculator 42. Moreover, stored in the storing device is a second computing program for executing a function of the second calculator 5. Stored in the second computing program are a functional information calculation program for executing a function of the functional information calculator 51 and a functional tumor degree calculation program for executing a function of the functional tumor degree calculator 52. Moreover, stored in the storing device is a third computing program for executing a function of the third calculator 6. Stored in the third computing program are a characteristics amount calculation program for executing a function of the feature amount calculator 61, a variations calculation program for executing a function of the change amount calculator 62, and a differentiation calculation program for executing a function of the differentiation calculator 63. Moreover, stored in the storing device is a display control program for executing a function of the display controller 8. The display control program includes a conversion program for executing a function of the converter 81. As the processing apparatus such as the CPU executes each program stored in the storing device, each function is executed. Note that one example of the "medical image processing program" is formed by the specific program, the first computing program, the second computing program, and the third computing program.

(Action)

An explanation is provided regarding a first action and a second action by means of the medical image processing apparatus 1 according to the present embodiment.

(First Action)

Figure 8:
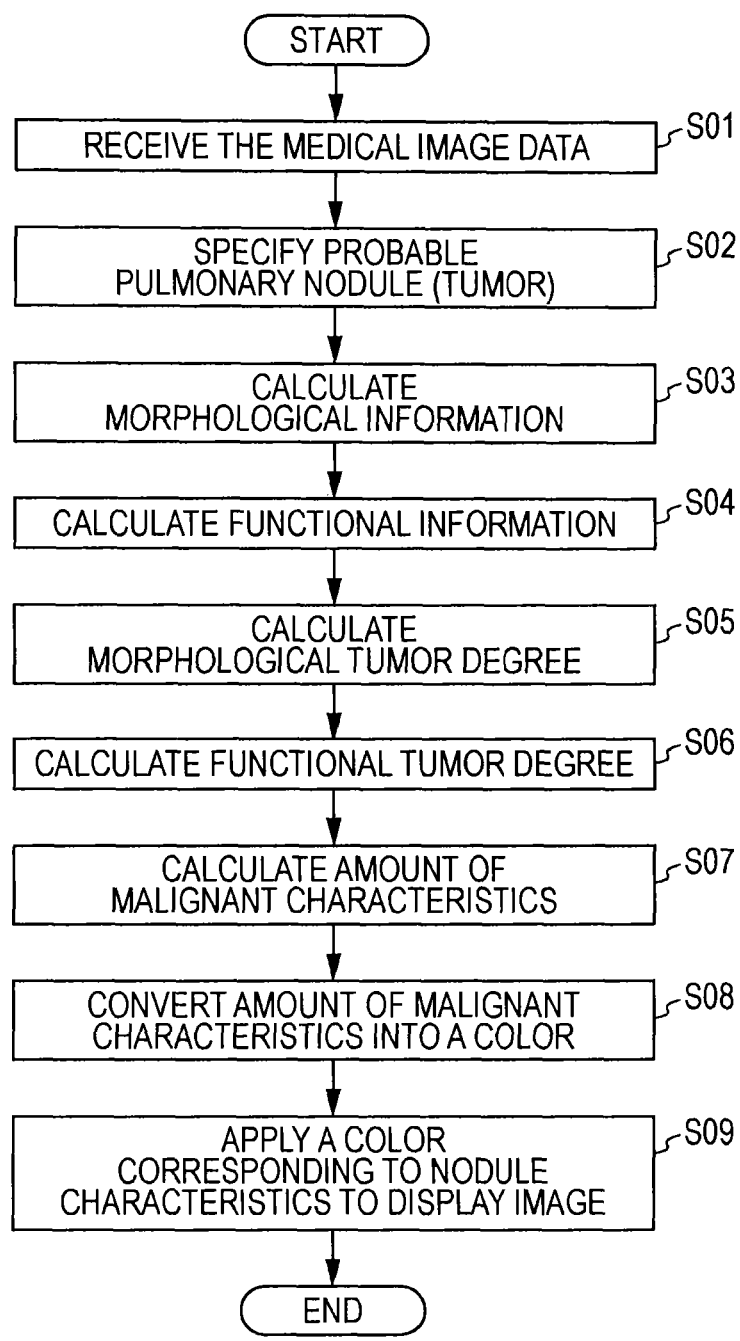
FIG. 8 is a flow chart showing an example of actions by means of the medical image processing apparatus according to the embodiment.

With reference to FIG. 8, an explanation is provided regarding a first action. FIG. 8 is a flow chart showing an example of actions by means of the medical image processing apparatus according to the present embodiment. The first action is executed if the position of the probable pulmonary nodule (tumor) is not specified and if the functional information is not calculated.

(Step S01)

The medical image processing apparatus 1 receives the medical image data from the medical imaging apparatus 90. The image storage 2 stores the medical image data. For example, the image storage 2 stores the non-contrast volume data 100 and the contrast volume data group 200 shown in FIG. 2. Note that the medical image processing apparatus 1 may also perform alignment for the non-contrast volume data 100 and the contrast volume data group 200.

(Step S02)

The specifying part 3 reads the non-contrast volume data 100 from the image storage 2 and specifies the probable pulmonary nodule (tumor) based on information such as the pixel value (CT value) of the non-contrast volume data 100.

(Step S03)

For example, the morphological information calculator 41 calculates the morphological information indicating the characteristics of the morphology of the probable pulmonary nodule based on the non-contrast volume data 100.
(Step S04)

For example, the functional information calculator 51 calculates functional information indicating the hemodynamics of the probable pulmonary nodule based on the contrast volume data group 200.

Processing of Step S03 and Step S04 may be performed in reverse sequence or simultaneously.
(Step S05)

Figure 4:
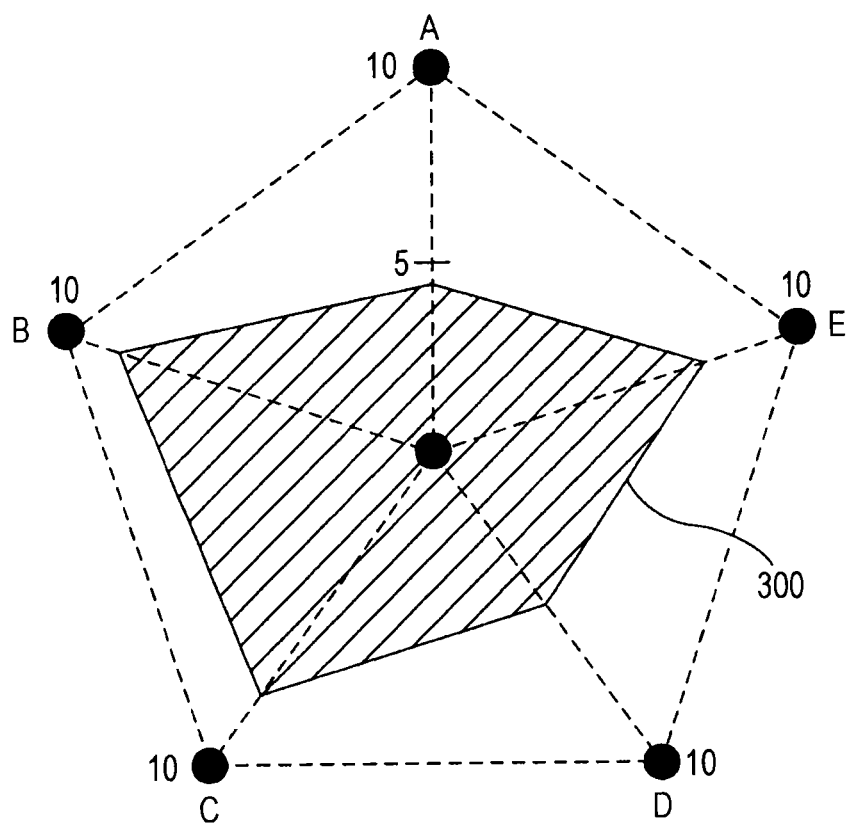
FIG. 4 is a radar chart showing the relationship between morphological information and morphological tumor degree.

The morphological tumor degree calculator 42 scores the morphological information and calculates the morphological tumor degree indicating the extent of the tumor with respect to the morphology of the probable pulmonary nodule. For example, as shown in FIG. 4, the morphological tumor degree calculator 42 creates a pentagon-shaped radar chart with the scores of five types of morphological information as variables. The morphological tumor degree calculator 42 plots the scores of the respective morphological information (standardized value) in the radar chart and connects the dots of the scores located next to each other. The morphological tumor degree calculator 42 calculates the area of the range 300 in which the dots of the scores located next to each other have been connected as the morphological tumor degree.
(Step S06)

The functional tumor degree calculator 52 scores the functional information and calculates the functional tumor degree indicating the extent of the tumor with respect to the hemodynamics of the probable pulmonary nodule. For example, as shown in FIG. 6, the functional tumor degree calculator 52 creates a pentagon-shaped radar chart with the scores of five types of functional information as variables. The functional tumor degree calculator 52 plots the scores of the respective functional information (standardized value) in the radar chart and connects the dots of the scores located next to each other. The functional tumor degree calculator 52 calculates the area of the range 400 in which the dots of the scores located next to each other have been connected as the functional tumor degree.

Processing of Step S05 and Step S06 may be performed in reverse sequence or simultaneously. Moreover, the medical image processing apparatus 1 may also perform processing of Step S05 subsequent to processing of Step S03 and perform processing of Step S06 subsequent to processing of Step S04.
(Step S07)

The feature amount calculator 61 calculates the nodule characteristics score (the amount of malignant characteristics) indicating the extent of the tumor of the probable pulmonary nodule based on the morphological tumor degree and the functional tumor degree.
(Step S08)

The converter 81 converts the value of the nodule characteristics score (the amount of malignant characteristics) into a color corresponding to the value.
(Step S09)

The display controller 8 applies a color corresponding to the nodule characteristics scores at the position of the probable pulmonary nodule above the image to cause the display 10 to display the image. For example, the image generator 7 creates the MPR image data by performing MPR processing on the non-contrast volume data 100. The display controller 8 applies a color corresponding to the nodule characteristics scores at the position of the probable pulmonary nodule above the MPR image to cause the display 10 to display the MPR image.

Note that the converter 81 may convert functional information such as blood flow into a color. For example, it changes color according to the functional information, creates in advance a color table in which the functional information and color are associated with each other, and stores it in advance in storage (not shown in the figures). The display controller 8 applies a color corresponding to functional information such as the blood flow at the position of the probable pulmonary nodule above the image and causes the display 10 to display the image.

By calculating the nodule characteristics scores (the amount of malignant characteristics) indicating the extent of the tumor based on the morphological information and the functional information, the medical image processing apparatus 1 with the above configuration allows nodules to be detected in which malignant transformation is difficult to specify from the morphological information alone. The medical image processing apparatus 1 according to the present embodiment allows the nodules which may turn malignant as shown by the nodule model 510 and the nodule model 511 in FIG. 7 to be detected. As a result, it is possible to specify the nodules with a possibility of turning malignant before they turn malignant, making it possible to specify the nodules with a possibility of turning malignant at an early stage. As above, based on the medical image processing apparatus 1 according to the present embodiment, it is possible to improve the accuracy (detection accuracy) of identifying the malignant transformation of probable pulmonary nodules (tumor).

Moreover, the medical image processing apparatus 1 according to the present embodiment applies a color corresponding to the nodule characteristic scores at the position of the probable pulmonary nodule above the image, allowing the operator to easily understand the extent of the tumor.

Moreover, the medical image processing apparatus 1 according to the present embodiment calculates the nodule characteristics scores based on the medical image data obtained by means of one type of medical imaging apparatus 90 (for example, a X-ray CT scanner), making it possible to conveniently identify malignant transformation of the probable pulmonary nodule. That is, according to the present embodiment, it is not necessary to use a plurality of diagnostic apparatuses, making it possible to improve convenience at hospitals.

(Second Action)

Figure 9:
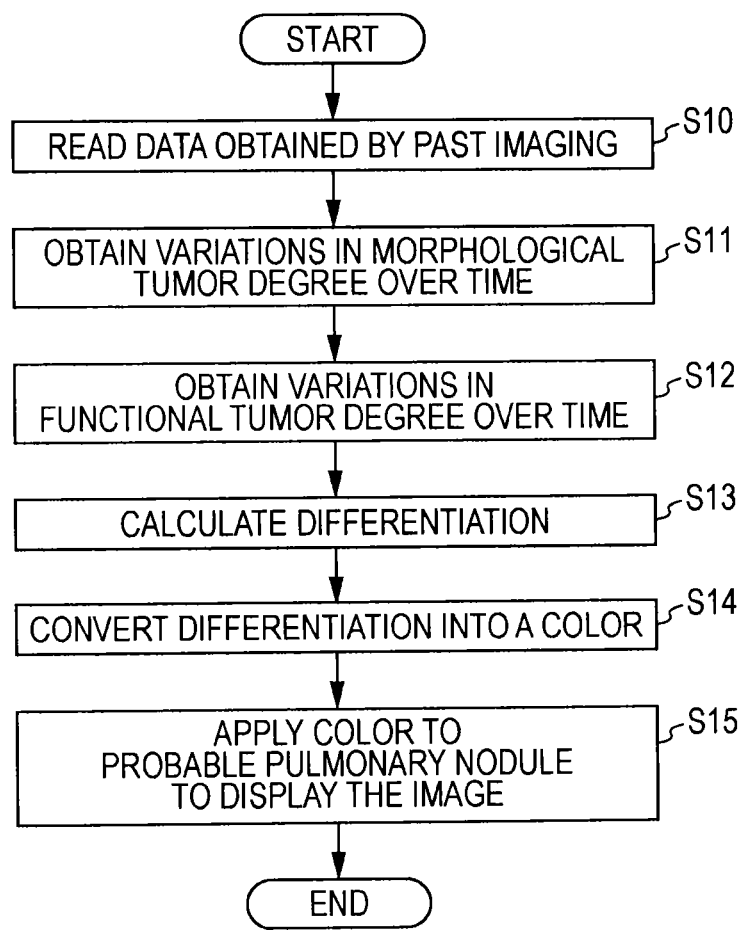
FIG. 9 is a flow chart showing an example of actions by means of the medical image processing apparatus according to the embodiment.

With reference to FIG. 8 and FIG. 9, an explanation is provided regarding a second action. FIG. 9 is a flow chart showing an example of actions by means of the medical image processing apparatus according to the embodiment. The second action is executed if imaging is performed in the past by means of the medical imaging apparatus 90 and if the morphological tumor degree and the functional tumor degree are calculated regarding past imaging. For example, if the first imaging is performed in the past by means of the medical imaging apparatus 90 and if data regarding the first imaging is already calculated, data regarding the first imaging is stored in the image storage 2. Specifically, the image storage 2 stores the morphological information, the morphological tumor degree, the functional information, the functional tumor degree, and the nodule characteristics score obtained by means of the first imaging. Second imaging is then performed by means of the medical imaging apparatus 90 and non-contrast volume data and a contrast volume data group are newly created.

(FIG. 8: Step S01 to Step S07)

If the second imaging is newly performed by means of the medical imaging apparatus 90, the medical image processing apparatus 1 executes processing from Step S01 to Step S07. Accordingly, the morphological information, the morphological tumor degree, the functional information, the functional tumor degree, and the nodule characteristics scores (the amount of malignant characteristics) are obtained regarding the second imaging.
(FIG. 9: Step S10)

The change amount calculator 62 reads the data obtained by means of the first imaging (past imaging) from the image storage 2. Specifically, the change amount calculator 62 reads the morphological information, the morphological tumor degree, the functional information, the functional tumor degree, and the nodule characteristics scores (the amount of malignant characteristics) regarding the first imaging from the image storage 2.
(Step S11)

The change amount calculator 62 obtains the variations in the morphological tumor degree over time by calculating the difference between the morphological tumor degree regarding the first imaging and the morphological tumor degree regarding the second imaging.
(Step S12)

The change amount calculator 62 obtains the variations in functional tumor degree over time by calculating the difference between the functional tumor degree regarding the first imaging and the functional tumor degree regarding the second imaging.

Processing of S11 and S12 may be performed in reverse sequence or simultaneously.
(Step S13)

The differentiation calculator 63 calculates the differentiation of the probable pulmonary nodule (tumor) based on the nodule characteristics score (the amount of malignant characteristics), the variations in morphological tumor degree over time, and the variations in the functional tumor degree over time regarding the second imaging.
(Step S14)

The converter 81 converts the value of the differentiation into a color corresponding to the value. The converter 81 may convert the variations in the morphological tumor degree over time into a color corresponding to the variations. The converter 81 may convert the variations in the functional tumor degree over time into colors corresponding to the variations.
(Step S15)

The display controller 8 applies a color corresponding to the differentiation at the position of the probable pulmonary nodule above the image to cause the display 10 to display the image. For example, the image generator 7 generates the MPR image data by performing MPR processing to the non-contrast volume data 100 obtained by means of the second imaging. The display controller 8 applies a color corresponding to the nodule characteristics score at the position of the probable pulmonary nodule above the MPR image to cause the display 10 to display the MPR image.

The display controller 8 may apply colors corresponding to the variations in the morphological tumor degree over time at the position of the probable pulmonary nodule above the image to cause the display 10 to display the image. The display controller 8 may apply colors corresponding to the variations in the functional tumor degree over time at the position of the probable pulmonary nodule above the image to cause the display 10 to display the image.

The medical image processing apparatus 1 with the above configuration calculates the differentiation based on the morphological information and functional information, allowing nodules to be detected in which malignant transformation is difficult to be specified only from the morphological information. That is, it is possible to specify nodules with a possibility of turning malignant before they turn malignant, making it possible to specify the nodules with a possibility of turning malignant at an early stage. In this way, the medical image processing apparatus 1 according to the present embodiment improves accuracy (detection accuracy) of identifying malignant transformation of probable pulmonary nodules (tumor).

Moreover, the medical image processing apparatus 1 according to the present embodiment applies a color corresponding to the differentiation at the position of the probable pulmonary nodule above the image, allowing the operator to easily understand the extent of the tumor.

If the medical image processing apparatus 1 does not execute the second action, the change amount calculator 62 and the differentiation calculator 63 may not have to be provided in the medical image processing apparatus 1.

If only the non-contrast volume data is generated without contrast imaging being performed in the first imaging, the first calculator 4 calculates the morphological tumor degree regarding the first imaging. In this case, the change amount calculator 62 may obtain the variations in the morphological tumor degree over time by calculating the difference between the morphological tumor degree regarding the first imaging and the morphological tumor degree regarding the second imaging.

The following combinations from (1) to (5) are included in the combination of the medical image data, which are the subject of processing in the present embodiment.
(1) The contrast volume data group including the plurality of contrast volume data.
(2) The non-contrast volume data and the contrast volume data group.
(3) The non-contrast volume data obtained by past imaging (the first imaging) and the contrast volume data obtained by new imaging (the second imaging).
(4) The contrast volume data group obtained by past imaging (the first imaging) and the contrast volume data group obtained by new imaging (the second imaging).
(5) The non-contrast volume data and the contrast volume data group obtained by means of past imaging (the first imaging) and the non-contrast volume data and the contrast volume data group obtained by new imaging (the second imaging)

The medical image processing apparatus 1 may execute processing by subjecting the medical image data according to any one combination from the above combinations (1) to (5). Moreover the operator may specify the combination of the medical image data, which are the subject of processing, using the operation part 11. In this case, the medical image processing apparatus 1 executes processing by subjecting the medical image data specified by the operator.

The medical image processing apparatus 1 according to the present embodiment may be included in the medical imaging apparatus 90. In this case, the medical imaging apparatus 90 generates the medical image data by imaging the subject and calculates the nodule characteristics scores (the amount of malignant characteristics) or the differentiation by executing the function of the medical image processing apparatus 1.

In the above embodiment, an explanation was provided for cases in which the invention was applied to an X-ray CT scanner; however, the invention is also applicable to multi-energy systems such as ultrasonic diagnostic equipment, X-ray angio system, MRI device, dual-energy system (DECT), and photon counting CT (PCCT). In these cases, the following content is included as functional information.
(1) Mass lesions in the abdominal parenchymal organs, the flow rate in the heart and vessels, the blood flow, elasticity, the degree of modification, movement, and the local cardiac output in the color Doppler test of the ultrasound diagnosis apparatus.

(2) The flow rate, the blood flow, the distribution volume (blood volume), movement, and the local cardiac output in blood flow analysis testing of the X-ray angio system.

(3) The blood flow, the distribution volume (blood volume), movement, and the local cardiac output in blood flow analysis testing of MR.

(4) The blood flow, the distribution volume (blood volume), the amount of fiber, the density of the subject substance, and the component ratio in the multi-energy system.

An embodiment of the invention has been described; however, the above embodiment has been presented as an example and it is not intended to limit the scope of the invention. These novel embodiments may be implemented in other various aspects and various omissions, replacements, and changes are possible within the gist of the scope of the invention. These embodiments or modifications are included in the scope or gist of the invention and are also included in the invention according to the scope of patent claims and the equivalent scope.

EXPLANATION OF THE SYMBOLS

1 Medical image processing apparatus
2 Image storage
3 Specifying part
4 First calculator
5 Second calculator
6 Third calculator
7 Image generator
8 Display controller
9 User interface (UI)
10 Display
11 Operation part
41 Morphological information calculator
42 Morphological tumor degree calculator
51 Functional information calculator
52 Functional tumor degree calculator
61 Feature amount calculator
62 Change amount calculator
63 Differentiation calculator
90 Medical imaging apparatus
100 Non-contrast volume data
110, 210 Probable pulmonary nodule
200 Contrast volume data group
201, 202, 203, 204, 205 Contrast volume data
300, 400 Range
500, 501, 502, 502, 503, 510, 511, 520, 521 Nodule model

What is claimed is:

1. A medical image processing apparatus comprising:
a medical imaging apparatus configured to image a subject by a single imaging modality to obtain morphological image data related to morphology of the subject and functional image data related to function of the subject;
a specifying part configured to specify a probable disease based on either or both of the morphological image data and the functional image data;
a first computing part configured to calculate morphological information indicating morphological characteristics of the specified probable disease based on the morphological image data;
a second computing part configured to calculate functional information of the specified probable disease based on the functional image data; and
a third computing part configured to calculate an amount of progress characteristics of indicating a progressing extent of the probable disease based on the morphological information and the functional information.

2. The medical image processing apparatus according to claim 1, wherein:
the medical imaging apparatus is configured to obtain a plurality of contrast enhanced image data as the functional image data by imaging the subject in which a contrast agent has been injected, and
the medical imaging apparatus is configured to obtain a plurality of non-contrast enhanced image data as the morphological image data by imaging the subject with no contrast agent injected therein.

3. The medical image processing apparatus according to claim 1, wherein:
the first computing part is further configured to calculate morphological disease progression indicating disease progress based on the morphological information;
the second computing part is further configured to calculate the functional disease progression indicating the disease progress based on the functional information; and
the third computing part is configured to calculate the amount of progress characteristics based on the morphological disease progression and the functional disease progression.

4. The medical image processing apparatus according to claim 3, wherein:
the third computing part is configured to obtain variations in the morphological disease progression over time by furthermore calculating a difference between the morphological disease progression and the morphological disease progression calculated in the past, and to obtain the variation in the functional disease progression over time by furthermore calculating the difference between the functional disease progression and the functional disease progression calculated in the past.

5. The medical image processing apparatus according to claim 4, wherein:
the third computing part is further configured to calculate differentiation of the probable disease based on the amount of progress characteristics, variation in the morphological disease progression over time, and variation in the functional disease progression over time.

6. The medical image processing apparatus according to claim 1, further comprising:
a display controller configured to cause a display to display medical images based on the morphological and functional image data and to apply a color corresponding to the amount of progress characteristics to the probable disease shown on the medical image.

7. The medical image processing apparatus according to claim 5, further comprising:
a display controller configured to cause a display to display a medical image based on the morphological and functional image data and to apply a color corresponding to the differentiation to the probable disease shown on the medical image.

8. The medical image processing apparatus according to claim 1, wherein:
the first computing part is configured to calculate at least one of either the size of the probable disease, the shape of the probable disease, the shape of the unevenness of the surface of the probable disease, and the inner structure of the probable disease, to obtain the morphological information.

9. The medical image processing apparatus according to claim 1, wherein:
the second computing part is configured to calculate at least one of the degree of elevation of the pixel values of the disease area, the blood flow of the disease area, the blood volume of the disease area, and the transit time of blood in the disease area to obtain the functional information.

10. A non-transitory computer-readable storage medium with a computer executable program stored thereon, wherein the program instructs a microprocessor to perform:
imaging a subject by a single imaging modality to obtain morphological image data related to morphology of the subject and functional image data related to function of the subject;
specifying a probable disease based on either or both of the morphological image data and the functional image data;
calculating morphological information indicating morphological characteristics of the probable disease specified based on the morphological image data;
calculating functional information of the probable disease specified based on the functional image data; and
calculating an amount of characteristics of progression indicating extent of the probable disease based on the morphological information and the functional information.

11. An X-ray CT scanner, comprising:
a medical imaging apparatus configured to image a subject by an X-ray CT scanning to obtain morphological image data related to morphology of the subject and functional image data related to function of the subject;
a specifying part configured to specify a probable disease based on either or both of the morphological image data and the functional image data,
a first computing part configured to calculate morphological information indicating morphological characteristics of the specified probable disease based on the morphological image data;
a second computing part configured to calculate functional information of the specified probable disease based on the functional image data; and
a third computing part configured to calculate an amount of progress characteristics indicating a progressing extent of the probable disease based on the morphological information and the functional information.

* * * * *